United States Patent
Mancini et al.

(10) Patent No.: US 9,936,943 B1
(45) Date of Patent: Apr. 10, 2018

(54) SUTURE PASSING SURGICAL DEVICE WITH ATRAUMATIC GRASPER PREVENTING ACCIDENTAL PERFORATIONS

(71) Applicants: Nicholas Mancini, Miller Place, NY (US); Jaimie Mancini, Miller Place, NY (US)

(72) Inventors: Nicholas Mancini, Miller Place, NY (US); Jaimie Mancini, Miller Place, NY (US)

( * ) Notice: Subject to any disclaimer, the term of this patent is extended or adjusted under 35 U.S.C. 154(b) by 238 days.

(21) Appl. No.: 14/820,097

(22) Filed: Aug. 6, 2015

Related U.S. Application Data (60) Provisional application No. 62/034,320, filed on Aug. 7, 2014.

(51) Int. Cl.
| | |
|---|---|
| *A61B 17/062* | (2006.01) |
| *A61B 17/04* | (2006.01) |
| *A61B 17/29* | (2006.01) |
| *A61B 17/34* | (2006.01) |

(52) U.S. Cl.
CPC ...... *A61B 17/0469* (2013.01); *A61B 17/0482* (2013.01); *A61B 17/29* (2013.01); *A61B 17/3468* (2013.01); *A61B 17/3474* (2013.01); *A61B 2017/047* (2013.01); *A61B 2017/2902* (2013.01); *A61B 2017/2947* (2013.01)

(58) Field of Classification Search
CPC . A61B 17/0468; A61B 17/0482; A61B 17/29; A61B 17/3415; A61B 17/3468; A61B 17/3474; A61B 17/0469; A61B 17/0483; A61B 17/0485; A61M 25/06

USPC ........ 606/148, 205–209, 139–141, 144–147
See application file for complete search history.

(56) References Cited

U.S. PATENT DOCUMENTS

| | | | |
|---|---|---|---|
| 349,791 | A | 9/1886 | Gibboney, Jr. |
| 373,372 | A | 11/1887 | King |
| 421,919 | A | 2/1890 | Fergen |
| 424,518 | A | 4/1890 | Van Norman |
| 652,175 | A | 6/1900 | Felson |

(Continued)

FOREIGN PATENT DOCUMENTS

| | | |
|---|---|---|
| EP | 0591991 | 4/1984 |
| EP | 0119967 | 9/1984 |

(Continued)

*Primary Examiner* — Kathleen Holwerda
(74) *Attorney, Agent, or Firm* — Locke Lord LLP; Scott D. Wofsy (57) ABSTRACT

A suture passing device includes a grasping mechanism and cannula having a sharp edge on a distal end. The grasper mechanism includes a hollow shaft slidably disposed within the cannula, with a first jaw fixedly secured thereto, and a second jaw pivotally coupled thereto, to pivot between a closed position wherein the second jaw engages the first jaw, and an open position. The slidable shaft permits the jaws to occupy a retracted position within the cannula, and an extended position. A plunger is slidably disposed within the hollow shaft, and pivotally coupled to the second jaw. A first handle is secured to the shaft, while a second handle is secured to the plunger, for jaw engagement/disengagement. The device also include means for locking sliding travel of the shaft relative to the cannula, after a full cycle of the slidable travel of the jaws between the extended and retracted positions has occurred.

18 Claims, 4 Drawing Sheets

(56) References Cited

U.S. PATENT DOCUMENTS

| | | |
|---|---|---|
| 659,422 A | 10/1900 | Shidler |
| 671,337 A | 4/1901 | Gibson |
| 919,138 A | 4/1909 | Drake et al. |
| 1,009,065 A | 11/1911 | Hahn |
| 1,293,565 A | 2/1919 | Smit |
| 1,449,087 A | 3/1923 | Bugbee |
| 1,464,832 A | 8/1923 | Richardson |
| 1,579,379 A | 4/1926 | Marbel |
| 1,635,066 A | 7/1927 | Wells |
| 1,641,077 A | 8/1927 | Fouguet |
| 1,656,467 A | 1/1928 | Blake |
| 1,815,725 A | 7/1931 | Pilling et al. |
| 1,822,330 A | 9/1931 | Ainslie |
| 1,855,546 A | 4/1932 | File |
| 1,856,721 A | 5/1932 | Nagelmann |
| 1,876,792 A | 9/1932 | Thompson |
| 1,933,024 A | 10/1933 | Nagelmann |
| 2,042,403 A | 5/1936 | Hrivnak |
| 2,065,659 A | 12/1936 | Cullen |
| 2,213,830 A | 9/1940 | Anastasi |
| 2,316,297 A | 4/1943 | Southerland et al. |
| 2,348,218 A | 5/1944 | Karle |
| 2,411,118 A | 11/1946 | Schuster |
| 2,414,882 A | 1/1947 | Longfellow |
| 2,434,133 A | 1/1948 | Volk |
| 2,577,240 A | 12/1951 | Findley |
| 2,579,192 A | 12/1951 | Kohl |
| 2,593,622 A | 4/1952 | Stanelle |
| 2,601,564 A | 6/1952 | Smith |
| 2,610,631 A | 9/1952 | Calicchio |
| 2,646,045 A | 7/1953 | Priestley |
| 2,738,790 A | 3/1956 | Todt et al. |
| 2,808,055 A | 10/1957 | Thayer |
| 2,880,728 A | 4/1959 | Rights |
| 2,895,478 A | 7/1959 | Post |
| 2,959,172 A | 11/1960 | Held |
| 3,013,559 A | 12/1961 | Thomas |
| 3,036,482 A | 5/1962 | Kenworthy et al. |
| 3,073,311 A | 1/1963 | Tibbs et al. |
| 3,090,386 A | 5/1963 | Curtis |
| 3,139,089 A | 6/1964 | Schwerin |
| 3,349,772 A | 10/1967 | Rygg |
| 3,393,687 A | 7/1968 | Whitman |
| 3,417,752 A | 12/1968 | Butler |
| 3,470,834 A | 10/1969 | Bone |
| 3,470,875 A | 10/1969 | Johnson |
| 3,638,653 A | 2/1972 | Berry |
| 3,687,138 A | 8/1972 | Jarvik |
| 3,716,058 A | 2/1973 | Tanner, Jr. |
| 3,752,516 A | 8/1973 | Mumma |
| 3,763,860 A | 10/1973 | Clarke |
| 3,807,407 A | 4/1974 | Schweizer |
| 3,840,017 A | 10/1974 | Violante |
| 3,842,824 A | 10/1974 | Neufeld |
| 3,842,840 A | 10/1974 | Schweizer |
| 3,856,018 A | 12/1974 | Perisse et al. |
| 3,871,379 A | 3/1975 | Clarke |
| 3,890,975 A | 6/1975 | McGregor |
| 3,901,244 A | 8/1975 | Schweizer |
| 3,946,740 A | 3/1976 | Bassett |
| 3,967,625 A * | 7/1976 | Yoon ............... A61B 17/12013 128/831 |
| 3,980,177 A | 9/1976 | McGregor |
| 3,985,138 A | 10/1976 | Jarvik |
| 3,990,619 A | 11/1976 | Russell |
| 4,027,608 A | 6/1977 | Arbuckle |
| 4,109,658 A | 8/1978 | Hughes |
| 4,161,951 A | 7/1979 | Scanlan, Jr. |
| 4,164,225 A | 8/1979 | Johnson et al. |
| 4,224,947 A | 9/1980 | Fukuda |
| 4,235,238 A | 11/1980 | Ogiu et al. |
| 4,236,470 A | 12/1980 | Stenson |
| 4,312,337 A | 1/1982 | Donohue |
| 4,326,531 A | 4/1982 | Shimonaka |
| 4,345,600 A | 8/1982 | Rothfuss |
| 4,345,601 A | 8/1982 | Fukuda |
| 4,373,530 A | 2/1983 | Kilejian |
| 4,384,406 A | 5/1983 | Tischlinger |
| 4,414,466 A | 11/1983 | Fischer et al. |
| 4,414,908 A | 11/1983 | Eguchi et al. |
| 4,417,532 A | 11/1983 | Yasukata |
| 4,423,729 A | 1/1984 | Gray |
| 4,440,171 A | 4/1984 | Nomoto et al. |
| 4,441,497 A | 4/1984 | Paudler |
| 4,448,194 A | 5/1984 | DiGiovanni et al. |
| 4,463,753 A | 8/1984 | Gustilo |
| 4,471,781 A | 9/1984 | Di Giovanni et al. |
| 4,493,323 A | 1/1985 | Albright et al. |
| 4,500,024 A | 2/1985 | DiGiovanni et al. |
| 4,509,516 A | 4/1985 | Richmond |
| 4,512,344 A | 4/1985 | Barber |
| 4,535,768 A | 8/1985 | Hourahane et al. |
| 4,539,474 A | 8/1985 | Li |
| 4,553,543 A | 11/1985 | Amarasinghe |
| 4,553,544 A | 11/1985 | Nomoto et al. |
| 4,557,265 A | 12/1985 | Andersson |
| 4,574,805 A | 3/1986 | Lerner |
| 4,580,563 A | 4/1986 | Gross |
| 4,590,929 A | 5/1986 | Klein |
| 4,596,249 A | 6/1986 | Freda et al. |
| 4,602,635 A | 7/1986 | Mulhollan et al. |
| 4,621,639 A | 11/1986 | Transue et al. |
| 4,621,640 A | 11/1986 | Mulhollan et al. |
| 4,633,869 A | 1/1987 | Schmeiding |
| 4,636,121 A | 1/1987 | Miller |
| 4,641,652 A | 2/1987 | Hutterer et al. |
| 4,643,178 A | 2/1987 | Nastari et al. |
| 4,660,559 A | 4/1987 | McGregor et al. |
| 4,662,068 A | 5/1987 | Polonsky |
| 4,716,893 A | 1/1988 | Fischer |
| 4,723,546 A | 2/1988 | Zagorski |
| 4,724,840 A | 2/1988 | McVay et al. |
| 4,739,751 A | 4/1988 | Sapega et al. |
| 4,741,330 A | 5/1988 | Hayhurst |
| 4,778,468 A | 10/1988 | Hunt et al. |
| 4,779,616 A | 10/1988 | Johnson |
| 4,781,190 A | 11/1988 | Lee |
| 4,787,377 A | 11/1988 | Laboureau |
| 4,790,312 A | 12/1988 | Capuano, Sr. et al. |
| 4,836,205 A | 6/1989 | Barrett |
| 4,846,799 A | 7/1989 | Tanaka et al. |
| 4,870,957 A | 10/1989 | Goble et al. |
| 4,871,289 A | 10/1989 | Choiniere |
| 4,881,537 A | 11/1989 | Henning |
| 4,884,572 A | 12/1989 | Bays et al. |
| 4,890,615 A | 1/1990 | Caspari et al. |
| 4,895,148 A | 1/1990 | Bays et al. |
| 4,899,743 A | 2/1990 | Nicholson et al. |
| 4,915,107 A | 4/1990 | Rebuffat et al. |
| 4,923,461 A | 5/1990 | Caspari et al. |
| 4,926,860 A | 5/1990 | Stice et al. |
| 4,932,961 A | 6/1990 | Wong et al. |
| 4,935,027 A | 6/1990 | Yoon |
| 4,950,285 A | 8/1990 | Wilk |
| 4,955,897 A | 9/1990 | Ship |
| 4,957,498 A | 9/1990 | Caspari et al. |
| 4,961,741 A | 10/1990 | Hayhurst |
| 4,976,715 A | 12/1990 | Bays et al. |
| 5,002,563 A | 3/1991 | Pyka et al. |
| 5,013,292 A | 5/1991 | Lemay |
| 5,015,250 A | 5/1991 | Foster |
| 5,026,350 A | 6/1991 | Tanaka et al. |
| 5,037,422 A | 8/1991 | Hayhurst et al. |
| 5,037,433 A | 8/1991 | Wilk et al. |
| 5,053,047 A | 10/1991 | Yoon |
| 5,059,201 A | 10/1991 | Asnis |
| 5,084,058 A | 1/1992 | Li |
| 5,085,661 A | 2/1992 | Moss |
| 5,087,263 A | 2/1992 | Li |
| 5,100,415 A | 3/1992 | Hayhurst |
| 5,100,418 A | 3/1992 | Yoon et al. |
| 5,100,421 A | 3/1992 | Christoudias |
| 5,120,318 A | 6/1992 | Nallapareddy |
| 5,123,913 A | 6/1992 | Wilk et al. |

(56) References Cited

U.S. PATENT DOCUMENTS

| | | | |
|---|---|---|---|
| 5,129,912 A | 7/1992 | Noda et al. |
| 5,133,723 A | 7/1992 | Li et al. |
| 5,149,329 A | 9/1992 | Richardson |
| 5,152,764 A | 10/1992 | Goble |
| 5,152,769 A | 10/1992 | Baber |
| 5,152,790 A | 10/1992 | Rosenberg et al. |
| 5,163,946 A | 11/1992 | Li |
| 5,174,087 A | 12/1992 | Bruno |
| 5,176,691 A | 1/1993 | Pierce |
| 5,178,629 A | 1/1993 | Kammerer |
| 5,181,919 A | 1/1993 | Bergman et al. |
| 5,188,636 A | 2/1993 | Fedotov |
| 5,192,287 A | 3/1993 | Fournier et al. |
| 5,201,739 A * | 4/1993 | Semm ............. A61B 17/2909 606/106 |
| 5,201,743 A | 4/1993 | Haber et al. |
| 5,201,744 A | 4/1993 | Jones |
| 5,211,650 A | 5/1993 | Noda |
| 5,211,655 A * | 5/1993 | Hasson ............. A61B 17/2909 600/564 |
| 5,217,471 A | 6/1993 | Burkhart |
| 5,217,486 A | 6/1993 | Rice et al. |
| 5,219,358 A | 6/1993 | Bendel et al. |
| 5,222,508 A | 6/1993 | Contarini |
| 5,222,962 A | 6/1993 | Burkhart |
| 5,222,976 A | 6/1993 | Yoon et al. |
| 5,224,955 A | 7/1993 | West |
| 5,234,443 A | 8/1993 | Phan et al. |
| 5,234,444 A | 8/1993 | Christoudias |
| 5,242,458 A | 9/1993 | Bendel et al. |
| 5,248,231 A | 9/1993 | Denham et al. |
| 5,250,054 A | 10/1993 | Li |
| 5,250,055 A | 10/1993 | Moore et al. |
| 5,254,126 A | 10/1993 | Filipi et al. |
| 5,257,637 A | 11/1993 | El Gazayerli |
| 5,259,846 A | 11/1993 | Granger et al. |
| 5,261,917 A | 11/1993 | Hasson et al. |
| 5,266,075 A | 11/1993 | Clark et al. |
| 5,269,783 A | 12/1993 | Sander |
| 5,269,786 A | 12/1993 | Morgan |
| 5,269,791 A | 12/1993 | Mayzels et al. |
| 5,273,024 A | 12/1993 | Menon et al. |
| 5,275,613 A | 1/1994 | Haber et al. |
| 5,281,234 A | 1/1994 | Wilk et al. |
| 5,282,809 A | 2/1994 | Kammerer et al. |
| 5,285,661 A | 2/1994 | Mathieu |
| 5,292,327 A | 3/1994 | Dodd et al. |
| 5,304,184 A | 4/1994 | Hathaway et al. |
| 5,304,185 A | 4/1994 | Taylor |
| 5,306,280 A | 4/1994 | Bregen et al. |
| 5,308,353 A | 5/1994 | Feurrier |
| 5,312,422 A | 5/1994 | Trott |
| 5,368,601 A | 5/1994 | Beurrier |
| 5,318,577 A | 6/1994 | Li |
| 5,320,632 A | 6/1994 | Heidmueller |
| 5,327,896 A | 7/1994 | Schmieding |
| 5,334,198 A | 8/1994 | Hart et al. |
| 5,356,419 A | 10/1994 | Chow |
| 5,364,408 A | 11/1994 | Gordon |
| 5,364,409 A | 11/1994 | Kuwabara et al. |
| 5,368,606 A | 11/1994 | Marlow et al. |
| 5,372,604 A | 12/1994 | Trott |
| 5,374,275 A | 12/1994 | Bradley |
| 5,376,096 A | 12/1994 | Foster |
| 5,382,257 A | 1/1995 | Lewis et al. |
| 5,387,221 A | 2/1995 | Bisgaard |
| 5,387,227 A | 2/1995 | Grice |
| 5,389,103 A | 2/1995 | Melzer et al. |
| 5,391,170 A | 2/1995 | McGuire et al. |
| 5,391,173 A | 2/1995 | Wilk |
| 5,393,302 A | 2/1995 | Clark et al. |
| 5,397,325 A | 3/1995 | Della Badia et al. |
| 5,403,328 A | 4/1995 | Shallman |
| 5,403,329 A | 4/1995 | Hinchcliffe |
| 5,409,494 A | 4/1995 | Morgan |
| 5,417,699 A | 5/1995 | Klein et al. |
| 5,417,701 A | 5/1995 | Holmes |
| 5,423,837 A | 6/1995 | Mericle et al. |
| 5,425,733 A | 6/1995 | Schmieding |
| 5,433,722 A | 7/1995 | Sharpe et al. |
| 5,439,467 A | 8/1995 | Benderev et al. |
| 5,439,474 A | 8/1995 | Li |
| 5,441,502 A | 8/1995 | Bartlett |
| 5,441,507 A | 8/1995 | Wilk |
| 5,449,367 A | 9/1995 | Kadry |
| 5,454,823 A | 10/1995 | Richardson et al. |
| 5,456,246 A | 10/1995 | Schmieding et al. |
| 5,462,562 A | 10/1995 | Elkus |
| 5,464,425 A | 11/1995 | Skiba |
| 5,466,243 A | 11/1995 | Schmieding et al. |
| 5,470,338 A | 11/1995 | Whitfield et al. |
| 5,474,565 A | 12/1995 | Trott |
| 5,476,470 A | 12/1995 | Fitzgibbons, Jr. |
| 5,478,344 A | 12/1995 | Stone et al. |
| 5,478,345 A | 12/1995 | Stone et al. |
| 5,480,406 A | 1/1996 | Nolan et al. |
| 5,486,185 A * | 1/1996 | Freitas ............. A61B 17/2909 606/142 |
| 5,496,331 A | 3/1996 | Xu et al. |
| 5,496,335 A | 3/1996 | Thomason et al. |
| 5,499,991 A | 3/1996 | Garman et al. |
| 5,501,688 A | 3/1996 | Whiteside et al. |
| 5,501,692 A | 3/1996 | Riza |
| 5,505,735 A | 4/1996 | Li |
| 5,507,755 A | 4/1996 | Gresl et al. |
| 5,507,757 A | 4/1996 | Sauer et al. |
| 5,520,696 A | 5/1996 | Wenstrom, Jr. |
| 5,520,703 A | 5/1996 | Essig et al. |
| 5,522,820 A | 6/1996 | Caspari et al. |
| 5,527,321 A | 6/1996 | Hinchliffe |
| 5,527,322 A | 6/1996 | Klein et al. |
| 5,531,757 A * | 7/1996 | Kensey ............. A61B 17/282 604/263 |
| 5,540,705 A | 7/1996 | Meade et al. |
| 5,545,170 A | 8/1996 | Hart |
| 5,549,613 A | 8/1996 | Goble et al. |
| 5,549,618 A | 8/1996 | Fleenor et al. |
| 5,549,636 A | 8/1996 | Li |
| 5,554,171 A | 9/1996 | Gatturna et al. |
| 5,562,683 A | 10/1996 | Chan |
| 5,562,686 A | 10/1996 | Sauer et al. |
| 5,562,687 A | 10/1996 | Chan |
| 5,562,696 A | 10/1996 | Nobles et al. |
| 5,565,122 A | 10/1996 | Zinnbauer et al. |
| 5,569,269 A | 10/1996 | Hart et al. |
| 5,569,299 A | 10/1996 | Dill et al. |
| 5,569,301 A | 10/1996 | Granger et al. |
| 5,571,090 A | 11/1996 | Sherts |
| 5,573,542 A | 11/1996 | Stevens |
| 5,575,801 A | 11/1996 | Habermeyer et al. |
| 5,578,044 A | 11/1996 | Gordon et al. |
| 5,584,835 A | 12/1996 | Greenfield |
| 5,586,986 A | 12/1996 | Hinchliffe |
| 5,591,179 A | 1/1997 | Edelstein |
| 5,591,180 A | 1/1997 | Hinchliffe |
| 5,601,557 A | 2/1997 | Hayhurst |
| 5,601,571 A | 2/1997 | Moss |
| 5,603,718 A | 2/1997 | Xu |
| 5,607,435 A | 3/1997 | Sachdeva et al. |
| 5,618,290 A | 4/1997 | Toy et al. |
| 5,618,304 A | 4/1997 | Hart et al. |
| 5,626,588 A | 5/1997 | Sauer et al. |
| 5,626,590 A | 5/1997 | Wilk |
| 5,630,825 A | 5/1997 | de la Torre et al. |
| 5,632,748 A | 5/1997 | Beck, Jr. et al. |
| 5,632,751 A | 5/1997 | Piraka |
| 5,643,266 A | 7/1997 | Li |
| 5,643,292 A | 7/1997 | Hart |
| 5,645,552 A | 7/1997 | Sherts |
| 5,649,939 A | 7/1997 | Reddick |
| 5,653,716 A | 8/1997 | Malo et al. |
| 5,658,299 A | 8/1997 | Hart |
| 5,662,658 A | 9/1997 | Wenstrom, Jr. |
| 5,662,665 A | 9/1997 | Ludwick |

(56) References Cited

U.S. PATENT DOCUMENTS

| | | |
|---|---|---|
| 5,665,096 A | 9/1997 | Yoon |
| 5,667,526 A | 9/1997 | Levin |
| 5,674,229 A | 10/1997 | Tovey et al. |
| 5,674,230 A | 10/1997 | Tovey et al. |
| 5,681,333 A | 10/1997 | Burkhart et al. |
| 5,690,652 A | 11/1997 | Wurster et al. |
| 5,690,653 A | 11/1997 | Richardson et al. |
| 5,690,677 A | 11/1997 | Schmieding et al. |
| 5,693,061 A | 12/1997 | Pierce et al. |
| 5,693,071 A | 12/1997 | Gorecki et al. |
| 5,695,522 A | 12/1997 | LeMaire, III et al. |
| 5,697,950 A | 12/1997 | Fucci et al. |
| 5,700,023 A | 12/1997 | Buelna et al. |
| 5,707,379 A | 1/1998 | Fleenor et al. |
| 5,709,694 A | 1/1998 | Greenberg et al. |
| 5,713,908 A | 2/1998 | Jameel et al. |
| 5,728,107 A | 3/1998 | Zlock et al. |
| 5,728,112 A | 3/1998 | Yoon |
| 5,728,113 A | 3/1998 | Sherts |
| 5,728,135 A | 3/1998 | Bregen et al. |
| 5,730,747 A | 3/1998 | Ek et al. |
| 5,735,862 A | 4/1998 | Jennings et al. |
| 5,741,278 A | 4/1998 | Stevens |
| 5,746,751 A | 5/1998 | Sherts |
| 5,746,753 A | 5/1998 | Sullivan et al. |
| 5,749,879 A | 5/1998 | Middleman et al. |
| 5,752,964 A | 5/1998 | Mericle |
| 5,755,728 A | 5/1998 | Maki |
| 5,797,927 A | 5/1998 | Yoon |
| 5,759,188 A | 6/1998 | Yoon |
| 5,766,183 A | 6/1998 | Sauer |
| 5,766,186 A | 6/1998 | Faraz et al. |
| 5,776,152 A | 7/1998 | Sekons |
| 5,792,152 A | 8/1998 | Klein et al. |
| 5,800,447 A | 9/1998 | Wenstrom, Jr. |
| 5,810,848 A | 9/1998 | Hayhurst |
| 5,810,852 A | 9/1998 | Greenberg et al. |
| 5,814,052 A | 9/1998 | Nakao et al. |
| 5,814,054 A | 9/1998 | Kortenbach et al. |
| 5,814,069 A | 9/1998 | Schulze et al. |
| 5,817,107 A | 10/1998 | Schaller |
| 5,817,111 A | 10/1998 | Riza |
| 5,824,009 A | 10/1998 | Fukuda et al. |
| 5,826,776 A | 10/1998 | Schulze et al. |
| 5,827,298 A | 10/1998 | Hart et al. |
| 5,827,299 A | 10/1998 | Thomason et al. |
| 5,830,220 A | 11/1998 | Wan et al. |
| 5,833,697 A | 11/1998 | Ludwick |
| 5,836,955 A | 11/1998 | Buelna et al. |
| 5,843,084 A | 12/1998 | Hart et al. |
| 5,843,099 A | 12/1998 | Nichols et al. |
| 5,843,100 A | 12/1998 | Meade |
| 5,846,254 A | 12/1998 | Schulze et al. |
| 5,855,311 A | 1/1999 | Hamblin et al. |
| 5,860,983 A | 1/1999 | Wenstrom, Jr. |
| 5,860,990 A | 1/1999 | Nobles et al. |
| 5,860,992 A | 1/1999 | Daniel et al. |
| 5,868,749 A | 2/1999 | Reed |
| 5,871,488 A | 2/1999 | Tovey et al. |
| 5,871,490 A | 2/1999 | Schulze et al. |
| 5,876,412 A | 3/1999 | Piraka |
| 5,879,371 A | 3/1999 | Gardiner et al. |
| 5,893,878 A | 4/1999 | Pierce |
| 5,895,395 A | 4/1999 | Yeung |
| 5,897,563 A | 4/1999 | Yoon et al. |
| 5,897,564 A | 4/1999 | Schulze et al. |
| 5,897,572 A | 4/1999 | Schulsinger et al. |
| 5,897,574 A | 4/1999 | Bonutti |
| 5,899,911 A | 5/1999 | Carter |
| 5,904,692 A | 5/1999 | Steckel et al. |
| 5,908,426 A | 6/1999 | Pierce |
| 5,908,428 A | 6/1999 | Scirica et al. |
| 5,910,148 A | 6/1999 | Reimels et al. |
| 5,918,604 A | 7/1999 | Whelan |
| 5,919,199 A | 7/1999 | Mers Kelly et al. |
| 5,925,064 A | 7/1999 | Meyers et al. |
| 5,928,252 A | 7/1999 | Steadman et al. |
| 5,928,267 A | 7/1999 | Bonutti et al. |
| 5,928,268 A | 7/1999 | Butwell et al. |
| 5,931,844 A | 8/1999 | Thompson et al. |
| 5,935,149 A | 8/1999 | Ek |
| 5,938,668 A | 8/1999 | Scirica et al. |
| 5,941,439 A | 8/1999 | Kammerer et al. |
| 5,944,724 A | 8/1999 | Lizardi |
| 5,947,982 A | 9/1999 | Duran |
| 5,951,559 A | 9/1999 | Burkhart |
| 5,954,732 A | 9/1999 | Hart et al. |
| 5,954,733 A | 9/1999 | Yoon |
| 5,957,937 A | 9/1999 | Yoon |
| 5,964,773 A | 10/1999 | Greenstein |
| 5,968,047 A | 10/1999 | Reed |
| 5,980,538 A | 11/1999 | Fuchs et al. |
| 5,980,557 A | 11/1999 | Iserin et al. |
| 5,984,932 A | 11/1999 | Yoon |
| 5,993,451 A | 11/1999 | Burkhart |
| 5,993,466 A | 11/1999 | Yoon |
| 5,993,467 A | 11/1999 | Yoon |
| 6,004,332 A | 12/1999 | Yoon et al. |
| 6,010,513 A | 1/2000 | Törmälä et al. |
| 6,017,358 A | 1/2000 | Yoon et al. |
| 6,024,747 A | 2/2000 | Kontos |
| 6,045,561 A | 4/2000 | Marshall et al. |
| 6,051,006 A | 4/2000 | Shluzas et al. |
| 6,059,800 A | 5/2000 | Hart et al. |
| 6,071,289 A | 6/2000 | Stefanchik et al. |
| 6,074,403 A | 6/2000 | Nord |
| 6,077,276 A | 6/2000 | Kontos |
| 6,080,180 A | 6/2000 | Yoon et al. |
| 6,086,601 A | 7/2000 | Yonn |
| 6,096,051 A | 8/2000 | Kortenbach et al. |
| 6,096,060 A | 8/2000 | Fitts et al. |
| 6,099,538 A | 8/2000 | Moses et al. |
| 6,117,144 A | 9/2000 | Nobles et al. |
| 6,126,665 A | 10/2000 | Yoon |
| 6,126,666 A | 10/2000 | Trapp et al. |
| 6,129,741 A | 10/2000 | Wurster et al. |
| 6,132,433 A | 10/2000 | Whelan |
| 6,143,004 A | 11/2000 | Davis et al. |
| 6,143,005 A | 11/2000 | Yoon et al. |
| 6,146,387 A | 11/2000 | Trott et al. |
| 6,159,224 A | 12/2000 | Yoon |
| 6,183,485 B1 | 2/2001 | Thomason et al. |
| 6,197,035 B1 | 3/2001 | Loubens et al. |
| 6,200,329 B1 | 3/2001 | Fung et al. |
| 6,217,592 B1 | 4/2001 | Freda et al. |
| 6,277,132 B1 | 8/2001 | Brhel |
| 6,322,570 B1 | 11/2001 | Matsutani et al. |
| 6,332,889 B1 | 12/2001 | Sancoff et al. |
| 6,355,050 B1 | 3/2002 | Andreas et al. |
| 6,358,258 B1 | 3/2002 | Arcia et al. |
| 6,436,109 B1 | 8/2002 | Kontos |
| 6,443,963 B1 | 9/2002 | Baldwin et al. |
| 6,454,777 B1 | 9/2002 | Green |
| 6,461,366 B1 | 10/2002 | Seguin |
| 6,475,135 B1 | 11/2002 | Levy |
| 6,511,487 B1 | 1/2003 | Oren et al. |
| 6,517,552 B1 | 2/2003 | Nord et al. |
| 6,551,330 B1 | 4/2003 | Bain et al. |
| 6,595,911 B2 | 7/2003 | LoVuolo |
| 6,599,298 B1 | 7/2003 | Forster et al. |
| 6,605,096 B1 | 8/2003 | Ritchart |
| 6,616,674 B2 | 9/2003 | Schmieding |
| 6,623,492 B1 | 9/2003 | Berube et al. |
| 6,638,283 B2 | 10/2003 | Thal |
| 6,679,895 B1 | 1/2004 | Sancoff et al. |
| 6,719,764 B1 | 4/2004 | Gellman et al. |
| 6,723,107 B1 | 4/2004 | Skiba et al. |
| 6,743,241 B2 | 6/2004 | Kerr |
| 6,770,084 B1 | 8/2004 | Bain et al. |
| 6,843,796 B2 | 1/2005 | Harari et al. |
| 6,896,686 B2 | 5/2005 | Webber |
| 8,133,255 B2 * | 3/2012 | Ravikumar ............ A61B 90/50 606/167 |
| 1,037,864 A1 | 9/2012 | Carlson et al. |

(56) References Cited

U.S. PATENT DOCUMENTS

| | | |
|---|---|---|
| 2002/0065526 A1 | 5/2002 | Oren et al. |
| 2002/0103493 A1 | 8/2002 | Thal |
| 2002/0128666 A1 | 9/2002 | Sancoff et al. |
| 2002/0138084 A1 | 9/2002 | Weber |
| 2002/0147456 A1 | 10/2002 | Diduch et al. |
| 2002/0173800 A1 | 11/2002 | Dreyfuss et al. |
| 2003/0023250 A1 | 1/2003 | Watschke et al. |
| 2003/0065337 A1 | 4/2003 | Topper et al. |
| 2003/0078599 A1 | 4/2003 | O'Quinn et al. |
| 2003/0078600 A1 | 4/2003 | O'Quinn et al. |
| 2003/0083695 A1 | 5/2003 | Morris et al. |
| 2003/0105474 A1 | 6/2003 | Bonutti |
| 2003/0144674 A1 | 7/2003 | Loubens et al. |
| 2003/0176874 A1 | 9/2003 | Sauer |
| 2003/0216756 A1 | 11/2003 | Klein et al. |
| 2003/0233106 A1 | 12/2003 | Dreyfuss |
| 2003/0233108 A1 | 12/2003 | Gellman et al. |
| 2004/0010273 A1 | 1/2004 | Diduch et al. |
| 2004/0073254 A1 | 4/2004 | Wyman et al. |
| 2004/0193185 A1 | 9/2004 | McBrayer |
| 2004/0199184 A1 | 10/2004 | Topper et al. |
| 2004/0249394 A1 | 12/2004 | Morris et al. |
| 2004/0260314 A1 | 12/2004 | Lizardi et al. |
| 2005/0043748 A1 | 2/2005 | Oren et al. |
| 2010/0191260 A1* | 7/2010 | Mohajer ............ A61B 17/3474 606/144 |
| 2015/0157317 A1* | 6/2015 | Bagaoisan ......... A61B 17/0485 606/148 |

FOREIGN PATENT DOCUMENTS

| | | |
|---|---|---|
| EP | 0140557 | 9/1984 |
| EP | 0174843 | 3/1986 |
| EP | 0207545 B1 | 1/1987 |
| EP | 315371 B1 | 5/1989 |
| EP | 535906 B1 | 4/1993 |
| EP | 0574707 A1 | 12/1993 |
| EP | 0778004 A1 | 6/1997 |
| EP | 0601676 | 3/1999 |
| EP | 903109 B1 | 3/1999 |
| EP | 1159920 A2 | 12/2001 |
| EP | 243221 A2 | 9/2002 |
| GB | 2081099 | 8/1980 |
| GB | 2081099 | 2/1982 |
| GB | 2260704 A | 4/1993 |
| GB | 2268690 | 1/1994 |
| WO | WO 8910096 | 11/1989 |
| WO | WO 9212674 | 8/1992 |
| WO | WO 9428801 | 12/1994 |
| WO | WO 9502363 | 1/1995 |
| WO | WO 9508958 | 4/1995 |
| WO | WO 9609796 | 4/1996 |
| WO | WO 9627331 | 9/1996 |
| WO | WO 9639946 | 12/1996 |
| WO | WO 9639948 | 12/1996 |
| WO | WO 9747246 | 12/1997 |
| WO | WO 9830151 | 7/1998 |
| WO | WO 9830152 | 7/1998 |
| WO | WO 9830153 | 7/1998 |
| WO | WO 9843545 | 10/1998 |
| WO | WO 9912480 | 3/1999 |
| WO | WO 9947050 | 9/1999 |
| WO | WO 0012013 | 3/2000 |
| WO | WO 0051498 | 9/2000 |
| WO | WO 0195809 A1 | 12/2001 |
| WO | WO 0243558 A2 | 6/2002 |

\* cited by examiner

SUTURE PASSING SURGICAL DEVICE WITH ATRAUMATIC GRASPER PREVENTING ACCIDENTAL PERFORATIONS

CROSS REFERENCE TO RELATED APPLICATIONS

This application claims priority on U.S. Provisional Application Ser. No. 62/034,320 filed on Aug. 7, 2014, the disclosures of which are incorporated herein by reference.

FIELD OF THE INVENTION

The present invention relates to improvements in surgical devices, and more particularly to apparatus which are capable of grasping and passing suture endoscopically.

BACKGROUND OF THE INVENTION

The passing of surgical suture through a patient's skin and into a body cavity is done during laparoscopic surgery (i.e., minimally invasive surgery) through relatively small incisions, usually about one centimeter or less in length. Since this technique offers a number of distinct advantages to the patient (e.g., shorter recovery times, and reduced pain, hemorrhaging, scarring, etc.), there have been a substantial number of surgical instruments developed to accommodate this type of procedure.

These instruments are typically a sharp, pointed, grasping device with the ability to puncture the skin of a body cavity and a fatty subcutaneous layer. However, these devices pose a danger to the patient by introducing a sharp object into a cavity where they inadvertently, and not infrequently, cause injury to tissue and organs that were not the subject of the procedure. In fact, one patient safety indicator rating as to the frequency of inadvertent punctures/lacerations is maintained by the Agency for Healthcare Research and Quality—its PSI-15 rating—which is available on the corresponding government web site. Also, with respect to laparoscopic procedures where two to five trocars (access points) are typically used, the FDA had issued a report on injuries related to such medical devices. The U.S. Food and Drug Administration had maintained a database of fatal and non-fatal injuries associated with trocar insertions, its MAUDE (Manufacturer and User Facility Device Experience) database, which served as a basis for the report (see also, "Surgical Pitfalls: Prevention and Management," by Stephen R. T. Evans, Saunders, 2008, pp. 97-100).

One such device is shown by U.S. Pat. No. 5,618,290 to Toy, the disclosures of which are incorporated herein by reference. The Toy device has a pointed end located distally from a needle shaft that could inadvertently puncture an organ or other tissue during the suturing process.

Accordingly, there is a need for an improved puncturing/suturing device that provides an added degree of safety with respect to the accidental perforation of organs and tissue during laparoscopic procedures. The present invention provides a solution to this long-felt but unmet need. The present invention, which can retract for insertion into the abdominal cavity and re-emerge and lock into place for patient safety as it enters the patients' intra-abdominal space, may also be utilized in alternate applications. The present invention may also be used as an added safety feature in a Veress Needle (needle and cannula device that enters the abdominal cavity percutaneously and then allows for CO2 gas to enter the abdominal space). Also, the creation of micro-laparoscopic instruments can utilize the retraction, re-emersion and locking feature for both percutaneous entry into the abdominal cavity and utilization of the instruments in the abdominal space. These laparoscopic instruments may include 32 cm×3 mm with distal ends that could have several instrument types, including blunt graspers, Maryland dissectors, blunt dissectors, clip appliers, monopolar or bipolar energy sources and Metzenbaum scissors.

OBJECTS OF THE INVENTION

It is an object of the invention to provide a surgical device that is capable of puncturing a patient's skin and tissue.

It is another object of the invention to provide a surgical device that is capable of passing suture through a cannula beneath the skin through the same portal created by an initial skin puncture.

It is a further object of the invention to provide a surgical device that may grasp and manipulate the suture and pass into and out of the abdominal cavity.

It is another object of the invention to provide a surgical device with a pair of grasper jaws that may initially be linearly deflected during the puncturing of a patient's skin, but is then subsequently biasing into an extended position and locked thereat to permit utilization.

It is also an object of the invention to provide a surgical device with a pair of grasper jaws that may be biased into an extended position and may thereat be driven in a scissors-type motion to permit suturing, but which may also retract to prevent injury to organs or other tissue as a result of accidental contact therewith.

Further objects and advantages of the invention will become apparent from the following description and claims, and from the accompanying drawings.

DETAILED DESCRIPTION OF THE INVENTION

Figure 1:
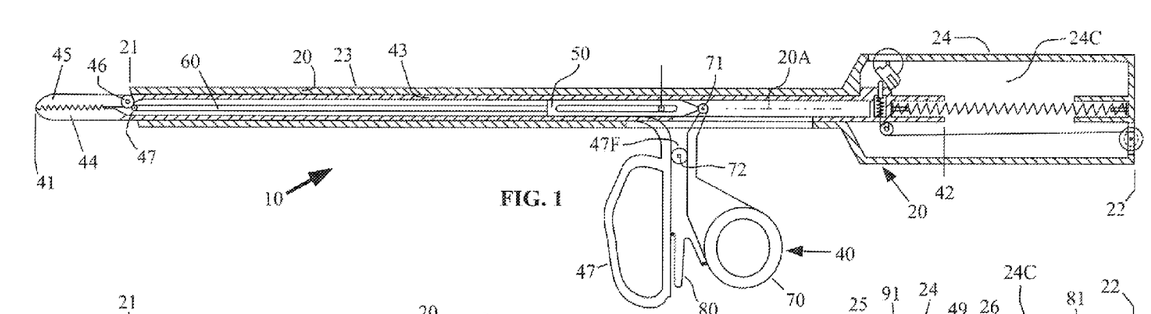
FIG. 1 is a cross-sectional view through a first embodiment of the suture passing device of the present invention, with the jaws shown biased into an extended position to protrude out from the cannula and in the closed position, and being unlocked axially with respect to the outer cannula.

FIG. 1 shows a first embodiment 10 of the suture passing surgical instrument/device of the present invention. The device 10 may include a cannula 20 that may span from a first end 21 to a second end 22. The cannula 10 may have a substantially cylindrical outer surface 23. The first end 21 of the cannula 20 may be formed at an angle θ with respect to the cannula axis 20A, to create a sharp edge that may be used to puncture the skin of the patient's body cavity to create a portal for entry of the grasper device during suturing. In addition to having a sharp edge resulting from the end 21 of the cannula being formed at an angle, the upper edge at the first end may protrude forward into a sharp point (not shown) to better enable puncturing of the skin.

At an axial position between the first end 21 and the second end 22 of cannula 20, the cylindrical outer surface 23 may transition, and may flare outwardly to form a handle portion 24. The handle portion 24 may be an in-line handle configured to be suitably grasped by the surgeon in order to apply a force to the beveled tip of the cannula 20 at first end 21, in order to puncture the skin of the patient's body cavity. The handle portion 24 may be particularly shaped to receive the user's fingers wrapped around the handle, with the person's thumb extended towards the distal end of the device, similar to the typical grip used on a golf club. Alternatively, the handle portion 24 may be cylindrical, and may be an offset of the cylindrical outer surface 23.

The cannula 20 may be hollow, and may have an inner cylindrical surface 231, which may be formed substantially concentric with the outer cylindrical surface 23. The inner cylindrical surface 231 may correspondingly transition proximate to the transition in the outer cylindrical surface 23, to form a cavity 24C in the handle portion 24.

Figures 2, 3:
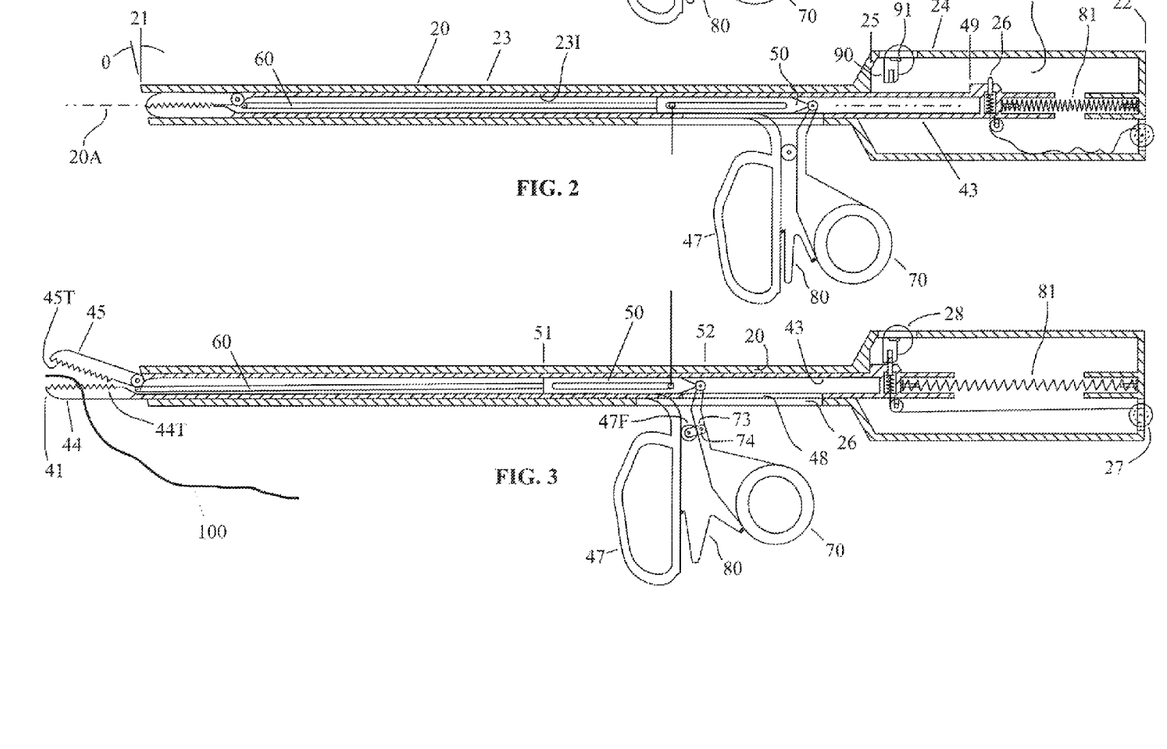
FIG. 2 is the suture passing device of FIG. 1, after a force is applied to the distal tip of the jaws to overcome the biasing to move the jaws into a retracted position within the cannula.
FIG. 3 is the suture passing device of FIG. 2, shown after the force has been removed from the jaws, which have been biased back into the extended position, and with the jaws now locked in the extended position with respect to the outer cannula, and shown in the open position.
Figure 3A:
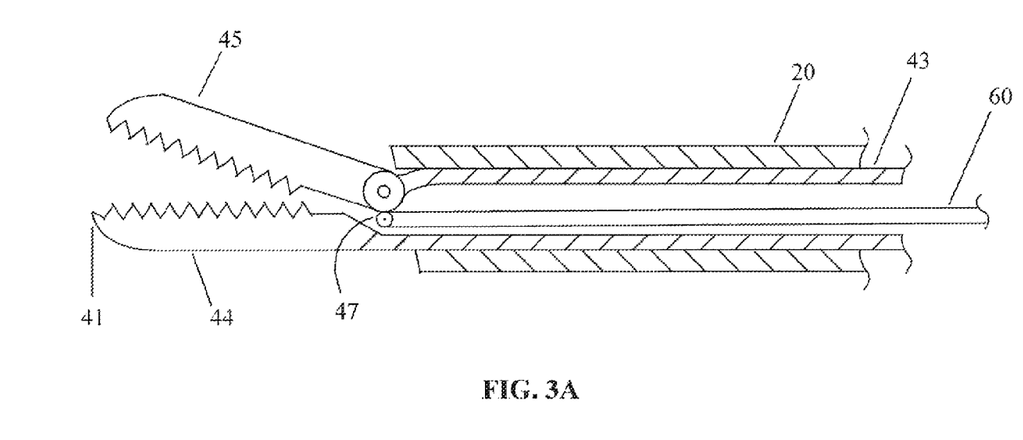
FIG. 3A is an enlarged detail view showing the jaws of the device as seen in FIG. 3.

A grasper mechanism 40 may include a shaft 43 that is slidably disposed within the hollow of cannula 20 defined by inner cylindrical surface 231. A lower portion of shaft 43 at its first end 41 may be formed into a non-pivoting lower jaw 44 (see FIG. 1 and FIG. 3), with teeth 44T formed thereon. The upper portion of the shaft 43 may be formed to terminate at a distance falling short of the first end 41, so that a hub portion of an upper jaw 45 may be pivotally coupled thereto at 46. The upper jaw 45 may also be formed with teeth 45T thereon. The upper jaw 45 may be pivotable between a closed position, in which its teeth 45T engage the corresponding teeth 44T of the lower jaw 44, as seen in FIG. 1, and one or more open positions, as seen in FIG. 3.

The shaft 43 may be biased into the extended position shown in FIG. 1 by a biasing means, which may be compression spring 81, or alternatively could be a tension spring. The biased travel may be limited to the extended position shown in FIG. 1 by a stop 49 on the shaft 43 contacting a corresponding interior wall surface 25 of the cannula 20. The spring may be retained within the cavity 24C of device 10 by one end of the spring being received within a recess on the end of the shaft 43, and a second end of the spring being received within a corresponding recess at the second end 22 of the cannula 20.

The shaft 43 may be hollow, and may have a plunger 50 slidably disposed therein. A first end of a rod 60, which may be flexible, may be pivotally or fixedly secured to a portion (e.g., a first end 51) of the plunger 50. The second end of the rod 60 may be pivotally attached to a hub of the upper jaw 45 at a lower peripheral protruding portion 45P of the hub, as seen in FIG. 1 (note that the use of a separate rod may be obviated by forming a rod portion integral with the plunger). It may therefore be seen that sliding and reverse sliding movements of the plunger 50 within shaft 43 may operate to correspondingly cause opening and closing of the upper jaw 45 with respect to the lower jaw 44.

To accomplish such sliding movement of the plunger 50 relative to shaft 43, an end of a finger handle 47 may be fixedly secured to a portion of the shaft, and a portion of the finger handle may protrude outwardly through an opening 26 in the cannula 20. The length of the opening 26 in the cannula 20 may permit unobstructed sliding movement of the finger handle 47 and shaft 43 combination, as seen within FIGS. 1-2 and discussed hereinafter. Furthermore, a thumb handle 70 may have an upper end be pivotally secured at 71 to a portion of the plunger 50, and a portion of the thumb handle may protrude outwardly through an opening 48 in the shaft 43, and through the opening 26 in the cannula 20. (Note that use of the terms "upper" and/or "lower" within this disclosure is only intended to be a relative descriptor with respect to the appearance of features of the device 10 that are shown in the drawing figures, and are not in any way intended to limit the orientation at which the device may be operated). Various different versions of the handles may be used, rather than just a finger handle/thumb handle combination (e.g., handle 47 may be configured to receive four fingers therein, as shown, or it may be smaller and may be segregated to only receive two fingers therein).

A spring means may bias the distal end of the pivotable thumb handle 70 (i.e., the portion of the handle farthest away from the shaft) towards the corresponding portion of the finger handle 47. The spring means is shown throughout the drawing figures as a leaf spring 80, however the described biasing may also be accomplished using a suitable helical spring. A central portion of the thumb handle 70 may be coupled to a fulcrum 47F that may be formed on the side of the finger handle 47 that is facing towards the thumb handle. Therefore, the biasing of thumb handle 70 relative to the finger handle 47 may cause pivoting of the thumb handle about the fulcrum 47F, and may correspondingly cause the reverse sliding movement of the plunger 50 within shaft 43 to normally move the upper jaw 45 into the closed position. To impart the sliding movement of the plunger 50 within shaft 43 to open the upper jaw 45, the thumb handle 70 may be pivotally coupled to the fulcrum 47F at 72, so that a force applied thereto to overcome the biasing, which would cause the lower portion of the thumb handle to separate and move distally away from the finger handle 47, and would also cause the upper end of the thumb handle to move in the opposite direction.

Therefore, when the leaf spring 80 has not been deformed to store elastic strain energy, and the lower finger portion of the finger handle 47 is in close proximity to the lower thumb portion of the thumb handle 70, as seen in FIG. 1, the upper jaw 45 may be in the closed position, with its teeth engaged with the teeth of the lower jaw 44.

When the thumb handle 70 of the device shown in FIG. 1 is actuated to pivot, to oppose the biasing of leaf spring 80 and deform it to store elastic strain energy, the resulting sliding movement imparted to the plunger 50 may cause the push rod 60, through its pivotal connection with the upper jaw 45, to drive the upper jaw to pivot relative to the shaft about point 46, and into the open position of FIG. 3.

With the thumb handle 70 configured to pivot directly about the fulcrum 47F, as seen in FIG. 1, with the associated kinematics normally causing a slight vertical displacement of the thumb handle's pivotal connection to the plunger, and because the upper connection at 71 is generally constrained to translate according to the sliding movement of the plunger 50 within shaft 43, this divergent loading could potentially cause jamming or cinching of the plunger. The potential for cinching could be reduced by using a loose clearance fit at the pivotal connection 71, and/or at the pivotal connection 72. Also, rather than simply utilizing a loose clearance fit that may affect sliding movement of the plunger 50, a vertical slotted opening in one of the parts to allow the pinned connection to slide therein would permit free pivoting, while accommodate small vertical movements to eliminate any opposition to the plunger's horizontal sliding movement.

Alternatively, rather than directly coupling the thumb handle 70 to the fulcrum 47F to pivot directly about point 72, a first end of a link 73 may instead be pivotally attached to the fulcrum 47F at that pivot point, and a second end of the link may be pivotally coupled to the thumb handle at pivot point 74, as seen in FIG. 3. This linkage arrangement may permit the smooth conversion of the complex movement of the thumb handle 70, into sliding movement of the plunger 50 within shaft 43.

To use the device 10 for suturing within the patient's body cavity, the surgeon may first grasp the suture 100 between the teeth 44T of the lower jaw and the teeth 45T of the upper jaw, by actuating the thumb handle 70 relative to the finger handle 47. Next the surgeon may grasp the in-line handle portion 24 of device 10 and aim the jaws 44/45 and first end 21 of cannula 20 to enter through the small surgical incision in the patient's outer skin. As the tip of the jaws 44/45 approach and contact the skin of the internal body cavity (e.g., abdominal cavity, thoracic cavity, etc.), the spring 81 may be compressed, and the jaws may be moved by such contact to withdraw into the hollow cannula, as seen in FIG. 2. After the skin of the body cavity has been pierced by the sharp edge at the first end 21 of cannula 20, and has passed through the layers of tissue to be within the cavity, pressure may be discontinued on the distal end of the device, at which time the blunt/rounded tip of the grasper formed by jaws 44/45 may re-emerge from the cannula as a result of biasing by spring 81. The surgeon may then manipulate the thumb handle 70 relative to finger handle 47 to commence suturing.

To thereafter lock the shaft 43 axially with respect to the cannula 20, a spring biased pin 26 on the shaft may be received within a recess of a pivotable lock member 90. The lock member may pivot about point 91, and may normally be biased into the position shown within FIG. 2 by a torsion spring. However, when the device 10 is initially ready to begin the procedure, the lock member 90 may be pre-positioned to be as seen in FIG. 1. When the jaws 44/45 contact the internal skin of the body cavity and the shaft slides for the jaws to retract within the cannula, the pin may cause the lock member 90 to further pivot counterclockwise against the biasing of the torsion spring, until the pin has moved clear of the lock member, at which time the torsion spring may bias the lock member to be as seen in FIG. 2. Once the jaws have entered the body cavity and have been biased to again be in the extended position, the pin will also have been advanced back into proximity with the recess in the lock member, and may itself be biased to be received therein, as seen in FIG. 3, to lock the shaft 43 axially with respect to the cannula 20. The locked arrangement shown in FIG. 3 may be reset, if/when desired, by sequenced rotating of dial 27, which may be coupled by wire to the biased pin 26 using a pulley, and rotating of dial 28, which may be coupled to lock member 91 and may cause the lock member to pivot.

Figure 4:
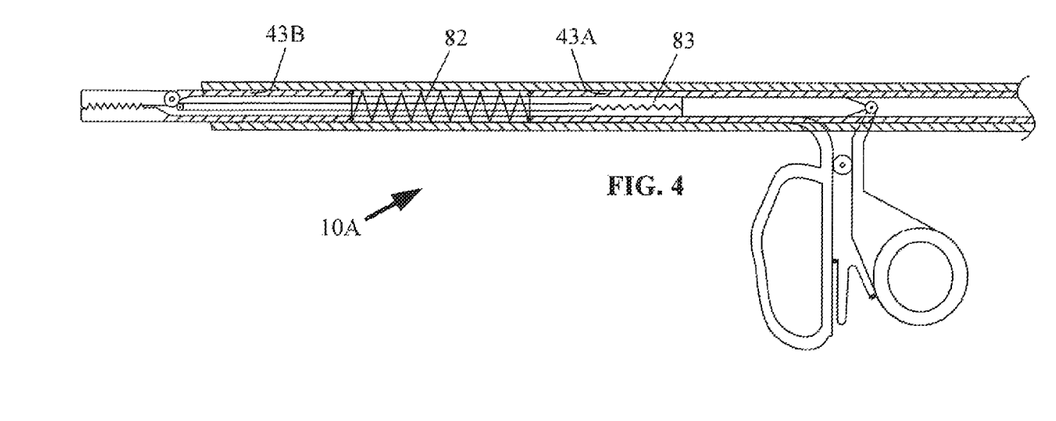
FIG. 4 is an alternate embodiment of the suture passing device of FIG. 1.
Figure 5:
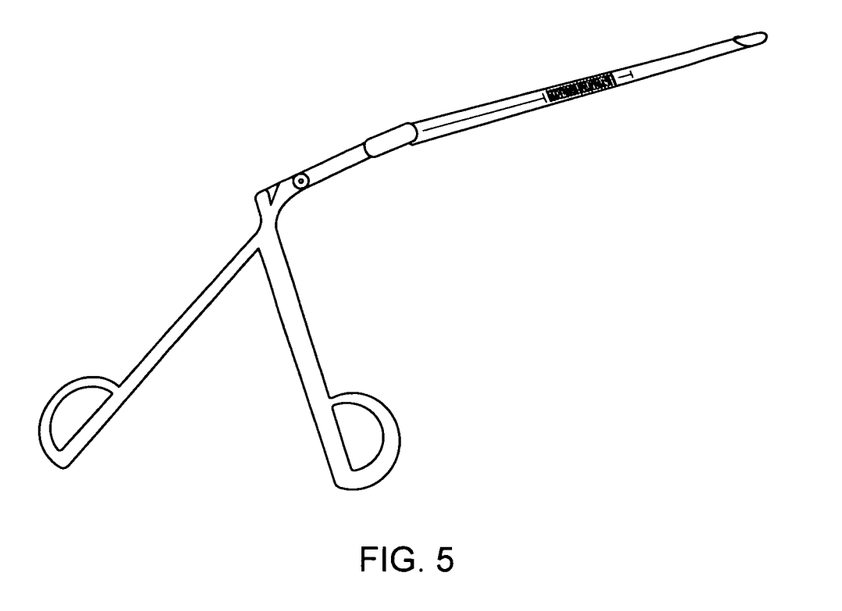
FIG. 5 is a side view of an alternate embodiment of the present invention.
Figure 5A:
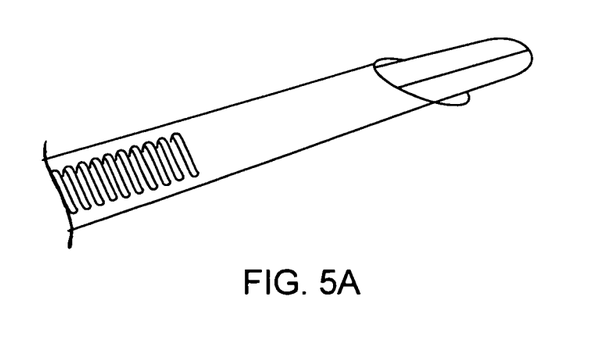
FIG. 5A shows an enlarged detail view of the distal end of the device of FIG. 5, with the tip shown in an extended and closed position.
Figure 5B:
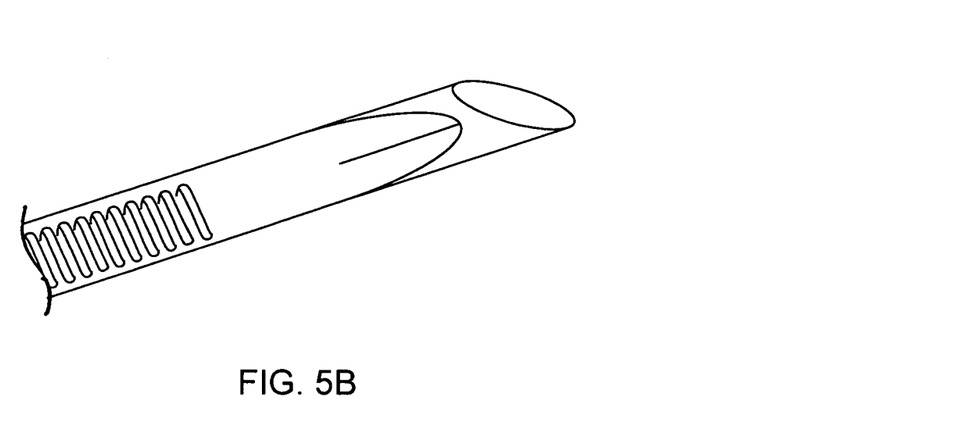
FIG. 5B shows the distal end of the device of FIG. 5A, but with the tip shown in a retracted position.
Figure 5C:
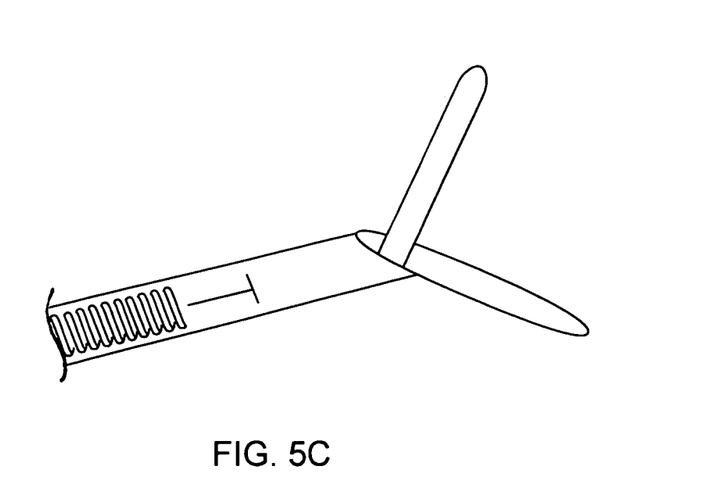
FIG. 5C shows the distal end of the device of FIG. 5A, but with the tip shown in an extended and open position.

An alternative embodiment 10A of the present invention is shown in FIG. 4; however, this feature may also be added to device 10 to provide an added level of safety thereto, to prevent the surgeon from accidentally puncturing an organ or other feature within the body cavity while suturing therein. As seen in FIG. 4, the shaft 43 may be split into two pieces—43A and 43B. The two pieces may be coupled with the ends of a spring 82 being respectively fixed to each of the ends of the shaft portions. Therefore, the thumb handle 70 and the finger handle 47 may be used to pivotally open and close the jaws 44/45 during suturing, but if the device is accidentally advanced too far into the depth of the cavity by the surgeon, where it contacts an organ or other sensitive tissue, the jaws 44/45 may partially retract within the cannula and cause compression of spring 82. Since the rod 60 would also serve to prevent the retraction of the jaws due to its direct connection with the finger handle 47, it may also be split into two pieces and a spring 83 may have its ends respectively connected to the ends of the two rod sections, as seen in FIG. 4. The springs 82 and 83 may be configured so that the jaws may only partially retract, which may be sufficient to provide tactile indication to the surgeon that an obstruction (i.e., an organ) was accidentally contacted, so that the surgeon may withdraw the device slightly.

The examples and descriptions provided merely illustrate a preferred embodiment of the present invention. Those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

What is claimed is:

1. A suture passing device for endoscopic surgery comprising:
    a) an elongated cannula defining an interior cylindrical bore and having opposed proximal and distal end portions, the distal end portion of the cannula defining a sharp beveled edge for puncturing through skin, the proximal end portion of the cannula extending distally from a cylindrical handle portion defining an interior cavity and a rear end wall;
    b) a grasper mounted for slidable travel relative to the elongated cannula and including an elongated hollow shaft supported within the interior cylindrical bore of the elongated cannula, a pair of cooperating grasping jaws operatively associated with a distal end portion of the hollow shaft and including a fixed lower jaw member and a pivoting upper jaw member configured to grasp a suture therebetween, a handle assembly for actuating the cooperating grasping jaws and including a fixed handle member and a pivoting handle member, and an elongated actuation rod and plunger extending through the hollow shaft to connect the pivoting jaw member to the pivoting handle member; and
    c) a biasing compression spring retained within the interior cavity of the handle portion of the cannula and disposed between a proximal end portion of elongated hollow shaft and the rear end wall of the handle portion of the cannula, wherein the grasper is mounted to travel between a withdrawn proximal position in which the cooperating grasping jaws are retracted within the distal end portion of the cannula against the bias of the compression spring and an extended distal position in which the cooperating grasping jaws extend out from the distal end portion of the cannula, beyond the beveled edge, under the bias of the compression spring.

2. The suture passing device recited in claim 1, wherein the proximal end portion of the elongated hollow shaft includes a stop surface for contacting a front end wall within the interior cavity of the handle portion of the cannula to limit the travel of the grasper.

3. The suture passing device recited in claim 1, wherein an opening is formed in a side wall of the cannula to accommodate unobstructed sliding movement of the handle assembly of the grasper relative to the cannula as the grasper travels between the distal and proximal positions.

4. The suture passing device recited in claim 1, further comprising a pivotable lock member disposed within the cavity of the handle portion of the cannula and having a recess for engaging a retractable pin positioned on the proximal end portion of the hollow shaft to automatically maintain the grasper in the extended distal position.

5. The suture passing device recited in claim 4, wherein the lock member is biased into an engagement position by a torsion spring.

6. The suture passing device recited in claim 5, wherein a rotatable dial is operatively associated with the handle portion of the cannula for pivoting the lock member out of the engagement position against the bias of the torsion spring.

7. The suture passing device recited in claim 4, wherein the retractable pin is biased into an engagement position by a coiled spring.

8. The suture passing device recited in claim 7, wherein a rotatable dial is operatively associated with the rear end wall of the handle portion of the cannula for selectively disengaging the retractable pin from the lock member.

9. The suture passing device recited in claim 8, wherein the rotatable dial is coupled to the retractable pin by a wire.

10. The suture passing device recited in claim 1, wherein the elongated actuation rod and plunger are integrally formed with one another.

11. The suture passing device recited in claim 1, wherein the pivoting handle member is pivotally secured to the plunger.

12. The suture passing device recited in claim 1, wherein a leaf spring is associated with the handle assembly of the grasper for biasing the pivoting handle member away from the fixed handle member, so that the cooperating grasping jaws of the grasper are maintained in a normally open position.

13. The suture passing device recited in claim 1, wherein the proximal end portion of the shaft has a recess for retaining a distal end portion of the biasing compression spring.

14. The suture passing device recited in claim 1, wherein a recess extends from the rear end wall of the handle portion of the cannula for retaining a proximal end portion of the biasing compression spring.

15. The suture passing device recited in claim 1, wherein the pivoting upper jaw member is pivotably connected to the distal end portion of the shaft.

16. The suture passing device recited in claim 1, wherein the elongated hollow shaft of the grasper is split into two separate elongated pieces that are coupled to one another by a coiled spring.

17. The suture passing device recited in claim 1, wherein the rod and plunger are split into two separate pieces that are coupled to one another by a coiled spring.

18. The suture passing device recited in claim 1, wherein the fixed lower jaw member and the pivoting upper jaw member both have blunt rounded tips.

* * * * *